(12) United States Patent
Sommer et al.

(10) Patent No.: US 12,016,709 B2
(45) Date of Patent: Jun. 25, 2024

(54) PATIENT PREPARATION FOR MEDICAL IMAGING

(71) Applicant: KONINKLIJKE PHILIPS N.V., Eindhoven (NL)

(72) Inventors: Karsten Sommer, Hamburg (DE); Sascha Krueger, Hamburg (DE); Peter Koken, Hamburg (DE); Julien Thomas Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/923,623

(22) PCT Filed: Mar. 9, 2022

(86) PCT No.: PCT/EP2022/055958
§ 371 (c)(1),
(2) Date: Nov. 7, 2022

(87) PCT Pub. No.: WO2022/194622
PCT Pub. Date: Sep. 22, 2022

(65) Prior Publication Data
US 2023/0414183 A1    Dec. 28, 2023

(30) Foreign Application Priority Data

Mar. 15, 2021    (EP) .................................... 21162638

(51) Int. Cl.
*G06K 9/00*        (2022.01)
*A61B 6/00*        (2006.01)
(Continued)

(52) U.S. Cl.
CPC ................ *A61B 6/04* (2013.01); *A61B 6/545* (2013.01); *G01R 33/283* (2013.01);
(Continued)

(58) Field of Classification Search
CPC .............. G06K 9/00; A61B 6/04; A61B 35/12
(Continued)

(56) References Cited

U.S. PATENT DOCUMENTS

2017/0100089 A1    4/2017  Chang et al.
2018/0070904 A1*   3/2018  Yu .............................. G06T 7/73
(Continued)

OTHER PUBLICATIONS

Lakshminarayanan, Balaji, Alexander Pritzel, and Charles Blundell. "Simple and scalable predictive uncertainty estimation using deep ensembles." In Advances in neural information processing systems, pp. 6402-6413. 2017.
(Continued)

*Primary Examiner* — Seyed H Azarian (57) ABSTRACT

A computer-implemented method for preparing a subject in medical imaging, comprising: obtaining a series of images of a region of interest comprising at least a part of the subject, wherein the series of images comprises at least a first image and at least a subsequent, second image (S10); determining a position of at least one landmark from the series of images, wherein the at least one landmark is anatomically related to a target anatomy (S20); determining a confidence level assigned to the position of the at least one landmark (S30); determining the position of the target anatomy based on the position of the at least one landmark, and the confidence level (S40); providing the position of the target anatomy for preparing the subject in medical imaging (S50).

20 Claims, 2 Drawing Sheets

(51) Int. Cl.
*A61B 6/04* (2006.01)
*A61B 34/20* (2016.01)
*G01R 33/28* (2006.01)
*G01R 33/54* (2006.01)
*G06T 7/00* (2017.01)

(52) U.S. Cl.
CPC .......... *G01R 33/543* (2013.01); *G06T 7/0012* (2013.01); *G06T 2207/10088* (2013.01)

(58) Field of Classification Search
USPC ........ 382/100, 103, 106–107, 128–133, 172, 382/173, 181, 189, 209, 219, 224, 254, 382/276, 285–291, 305, 318; 378/4, 21, 378/28
See application file for complete search history.

(56) References Cited

U.S. PATENT DOCUMENTS

| | | | |
|---|---|---|---|
| 2018/0116518 A1* | 5/2018 | Rinck | G01R 33/4808 |
| 2019/0274582 A1* | 9/2019 | Zeller | A61B 5/684 |
| 2020/0279371 A1 | 9/2020 | Wenzel et al. | |
| 2021/0104043 A1* | 4/2021 | Crawford | G06T 7/0014 |
| 2022/0172398 A1* | 6/2022 | Wu | G06T 7/75 |
| 2023/0102908 A1* | 3/2023 | Govari | G06T 11/00 |
| | | | 382/128 |

OTHER PUBLICATIONS

Gal, Yarin, and Zoubin Ghahramani. "Dropout as a bayesian approximation: Representing model uncertainty in deep learning." In international conference on machine learning, pp. 1050-1059. 2016.

International Search Report and Written Opinion from PCT/EP2022/055958 dated May 13, 2022.

Toshev et al "Deep Pose: Human Pose Estimation via Deep Neural Networks" arXiv:1312.4659v3 [cs.CV] Aug. 20, 2014.

Vivek Sing et al "Estimating a Patient Surface Model for Optimizing the Medical Scanning" International Conference on Medical Image Computing and Computer-Assisted Intervention, 2014, pp. 472-479.

Chu et al "Human Pose Estimation Using Deep Convolutional Densenet Hourglass Network with Intermediate Points Voting" 2019 IEEE International Conference on Image Processing (ICIP), Taipei, Taiwan, 2019, pp. 594-598, doi: 10.1109/ICIP.2019.8803789.

Achilles et al "Patient MoCap: Human Pose Estimation under Blanket Occlusion for Hosptial Monitoring Applications" MICCAI 2016 International Conference on Medical Image Computing and Computer-Assisted Intervention MICCAI 2016: Medical Image Computing and Computer-Assisted Intervention—MICCAI 2016 pp. 491-499.

* cited by examiner

PATIENT PREPARATION FOR MEDICAL IMAGING

CROSS REFERENCE TO RELATED APPLICATIONS

This application is a U.S. national phase application of International Application No. PCT/EP2022/055958 filed Mar. 9, 2022, which claims the benefit of EP Application Serial No. 21162638.7 filed on Mar. 15, 2021.

FIELD OF THE INVENTION

The present invention relates to medical imaging, and in particular to a computer-implemented method for preparing a subject in medical imaging, a device for preparing a subject in medical imaging, an imaging system, and a computer program element.

BACKGROUND OF THE INVENTION

Medical imaging is a key technology in modern medicine. The medical imaging workflow requires trained personnel to operate the imaging units, such as a magnetic resonance imaging (MRI) system. Preparation of a subject and/or the imaging unit in medical imaging is time consuming and crucial for the quality of medical images. The personnel is therefore challenged with numerous and different tasks. Such tasks comprise, for example, alignment of a subject and medical imaging unit, positioning of medical imaging equipment adjacent to the subject, adapting the imaging unit, and/or documenting the workflow etc.

Each step requires attention of the personnel and time. Furthermore, each step may lead to potential errors.

US patent application 2018/0070904A1 discloses a motion tracking system that overlays tracking data over imaging data of a patient and displaying them together. The tracking data is generated by estimating patient motion from the data US patent application 2018/116518A1 discloses providing preparatory data for an MRI procedure by using a depth map of the patient on a patient support using a time-of-flight camera.

SUMMARY OF THE INVENTION

Therefore, there may be a need for a method for preparation of a patient in medical imaging, in particular a need for an improved method for preparation of the patient in medical imaging. The object of the present invention is solved by the subject-matter of the independent claims, wherein further embodiments are incorporated in the dependent claims.

According to a first aspect, there is a computer-implemented method for preparing a subject in medical imaging provided, comprising: obtaining a series of images of a region of interest comprising at least a part of the subject, wherein the series of images comprises at least a first image and at least a subsequent, second image; determining a position of at least one landmark from the series of images, wherein the at least one landmark is anatomically related to a target anatomy; determining a confidence level assigned to the position of the at least one landmark; determining the position of the target anatomy based on the position of the at least one landmark, and the confidence level; providing the position of the target anatomy for preparing the subject in medical imaging.

The term subject is to be understood broadly in the present case and comprises any humans and any animals. The term medical imaging is to be understood broadly in the present case and comprises any imaging process that is configured to image a region of interest in terms of medical images to be further used for e.g. examinations. Medical imaging may comprise CT imaging, MRI, X-Ray imaging. Medical imaging may particularly comprise in the present case MRI. A series of images means in the present case a plurality of single images. The single images may be obtained in certain temporal intervals. The certain temporal intervals relate to frame rates. A frame rate means in the present case a number of obtained images in one second. In the present case, the frame rate may be 1, 10, 24, 30, 35, or 60. The images may be obtained by a camera that is arranged above the subject and/or the medical imaging device such that the obtained image comprises a region of interest. The camera may also be arranged differently, for example adjacent to the subject such that a side view of the region of interest is obtained. The camera may preferably be a digital light photo camera or a digital light video camera. The images may be obtained from one or more cameras. The term region of interest is to be understood broadly in the present case and comprises parts of the subject on the surface of the subject, such as the torso, back, extremities, joints, etc. or inside the subject, such as inner organs. For example, the region of interest may be a kneecap that is visible from the surface. In another example, the region of interest may be a liver that is inside the subject and therefore invisible from the view of a digital light camera or a digital light video camera. The region of interest may be obstructed or hidden by, for example, a medical cover, an imaging equipment (such as MRI coil), a medical assistant, the subject itself (leg above the desired kneecap), human tissue above an organ (such as the liver). The term position means in the present case an x, y, z position in the image that indicates an x, y, z position in an imaging unit and/or imaging system such as an MRI or a CT. The position may further mean in the present case a content or extension of the region of interest in the image. For example, the position may relate to the volume dimensions of a liver. The volume dimension in the image may relate to the volume dimension and/or position in a coordinate system of an imaging unit or imaging system such as an MRI, a CT, or an X-Ray system. The term landmark is to be understood broadly in the present case and means a reference point provided by the subject itself. Preferably, the landmark may be a physical marker of the subject itself, such as a body part of the subject, e.g. a bone, a head, a nose, or a rip. The physical marker may be concise enough to be detected in an image. In other words, the physical marker can be easily detected in case of visibility in an image. The term anatomically connected means in the present case that a movement or shift of a landmark influences or affects a position of the target anatomy. For example, if the position of a kneecap changes, also the position of a corresponding lower leg bone changes because of their anatomic connection. In other words, the target anatomy and the landmarks show a kinematic chain. For example, the position of an organ such as the liver as target anatomy depends on the position of the adjacent rips that may be the landmarks in this example. The term target anatomy means in the present case the desired anatomy of which the position has to be determined. Examples for target anatomies are bones, joints, organs, tissue areas, blood vessels, but also tumors or irregularities detected in former treatments of the subject. The term confidence level means in the present case a measure for certainty of a position of a landmark. In other words, the confidence level relates to the reliability of the position. The confidence level may be in a range between 0 to 1, wherein 0 relates to a low reliability and 1 to high reliability. The confidence level may be estimated based on an entropy or a variance of predictions of the position in the at least one image. The term preparing of the medical subject in medical imaging is to be understood broadly in the present case and comprises any tasks related to the medical imaging process, such as positioning of the subject on the table, determination of the scan position, placement of imaging equipment on or at the subject, adjusting the control of an imaging unit or an imaging system based on the determined position, or ensuring compliance with safety guidelines. The information of the position of target anatomy may be transmitted to a control of the imaging system or the imaging unit. The information of the position of the target anatomy may displayed on a screen to guide a medical assistant.

In other words, the disclosed computer-implemented method for preparing a subject in medical imaging is based on the finding that there is a difficulty for medical assistants to determine precisely and quickly the position of the target anatomy of the subject in a preparation phase in medical imaging. The knowledge of an exact position is crucial for adapting the medical imaging unit or medical imaging system. Furthermore, the knowledge of the exact position of the target anatomy is crucial for preparing the subject, such as placing imaging equipment on or at the subject. However, the target anatomy, such as the liver, may be hidden for the camera, such that the position of the target anatomy, e.g., liver, is not directly determined, instead the position of the liver is indirectly determined from neighboring landmarks that are anatomically related to the target anatomy. For example, three landmarks, namely head, rip and hip are tracked in order to determine their respective positions and based on their position information the position of the liver is determined There may occur some reliability issues regarding the localization of the three landmarks. For example, a medical assistant may occlude the view between the camera and the hip of the subject. To detect such reliability issues is crucial to determine the confidence levels of the landmark. The determined confidence level of the hidden landmark in the image may decrease. To solve this reliability issue a previous image with a high confidence level for this landmark is used. Hence, it is possible to derive the position of the target anatomy with a high accuracy, a high reliability even in case of obstacles in the view of the camera. This increases the productivity of the medical imaging process as the medical assistant does not have to manually carry out the task of determining the position of the target anatomy. Furthermore, it increases the quality of medical imaging as the position of the target anatomy is precisely calculated by the disclosed method. The determining of the position is to be understood broadly and means in the present case a localization, in particular a localization of the landmark and/or of the target anatomy.

According to an embodiment the position of the target anatomy is, in case that the confidence level of the at least one landmark in the second image is below a predetermined threshold, determined from the at least one landmark in the first image. The predetermined threshold may be 0.85, preferably 0.9, and particularly preferred 0.95. In other words, if the current image that is the newest available image provides only a poor confidence level for the position of the at least one landmark, the method does not use the position of the landmark in the current image for determining the position of the target anatomy. Instead, the method uses the position of the landmark of a previous image. As the method considers a series of images, it is clear that in case of several successive images with a low confidence level for the at least one landmark, the last image with a high confidence level for the at least one landmark is used to determine the position of the target anatomy. In other words, the first image and the second do not necessarily have to be directly successively obtained, there may be several images in between. This may be advantageous as for an at least partial occlusion of the subject the landmarks are corrected by the method and lead to a proper determination of the position of the target anatomy.

According to an embodiment, determining the position of the target anatomy may comprise further determining a shift of the position of the at least one landmark between the first image and the second image. The term shift means in the present case a change of the position of the at least one landmark between the first image and the second image. The shift of the position of the at least one landmark may serve as a checkup possibility for a determined landmark with a confidence level near the threshold in the second image. Furthermore, the shift may lead to a more accurate determination of the position of the target anatomy, because from the position of the landmark in the first image possible ambiguities of the position of the landmark in the second image may be excluded. The shift may further be determined by calculating a mean or an average value of both positions in the first and second image. This may be advantageous in order to reduce errors occurring during the image acquisition process as they may smooth outliers. The shifts of more than one landmark, e.g. five landmarks, may be used in case of an occlusion of a further landmark, e.g. a sixth landmark, to determine a shift of the position of the further landmark, wherein the determining is based on an average of the shifts of the five landmarks. This may be advantageous to increase the localization accuracy of the position of the target anatomy.

According to an embodiment, the position of the target anatomy may be, in case that the confidence level of the at least one landmark in the second image is above the predetermined threshold, determined either from a shift of the position of the at least one landmark between the first image and the second image, or from the at least one landmark in the second image. In other words, based on the determined confidence level of the at least one landmark in the second image two possibilities for determining the position of the target anatomy are available. In the first possibility the position of the at least one landmark is determined based on the shift of the position of the at least one landmark between the first and second image, which may be advantageous to correct/adapt the position of the target anatomy from the first image to the second image. The second possibility is determine the anatomy based on the determined landmark in the second image. This may be advantageous in terms of calculation efficiency as only one image is required. The method may further comprise the determining of a target anatomy confidence level for the position of the target anatomy. The above-mentioned possibilities to determine the position of the landmark in case of the confidence level above a predetermined threshold may also take into account a confidence level of the position of the target anatomy. Both possibilities may be performed and as a result, the position of the target anatomy with the highest confidence level may be chosen. This may be advantageous to increase the localization accuracy of the position of the target anatomy.

In an embodiment, based on the determined confidence level a weighting factor for a shift of the position of the at least one landmark may be determined, and wherein the weighting factor is used for determining the position of the target anatomy. The determining of the shift of the position of the landmark may lead to an uncertainty. Hence, it is useful to consider this uncertainty by weighting factors. A possibility is to use the confidence level of the position of the at least one landmark in the corresponding image (e.g. from the second image by a shift from the first image to the second image). This may be advantageous in terms of increasing the accuracy of determining the position of the target anatomy.

In an embodiment, the at least one landmark may be selected in dependency of a presence of the landmark in the series of images. The term presence means in the present case that the landmark is visible for a camera that is implemented for example above the region of interest. The presence may be compromised by an obstacle, e.g. medical assistant. The position of the target anatomy can be described by a quantity x from 1 up to n landmarks, wherein n is a finite number. The method may select for the target anatomy in the beginning of the preparation phase from the quantity x merely the visible landmarks in order to determine the position of the target anatomy. The selection of the landmarks may be carried out several times during the preparation phase.

In an embodiment, the target anatomy may be hidden by an obstacle. The term obstacle is to be understood broadly in the present case and comprises any element, which is configured to hide the target anatomy. The term may comprise a part of the subject itself, a medical assistant, a medical equipment, etc. In an embodiment, the at least one landmark may be hidden by an obstacle.

In an embodiment, the position of the target anatomy may be determined from a plurality of landmarks, i.e. two or more landmarks. This may be advantageous in case that one or more landmarks are hidden by an obstacle, while one or more further landmarks may still be visible for the camera. This may further be advantageous as more landmarks may lead to more precise determining of the position of the target anatomy. It should be noted that in case of several landmarks also for each landmark a corresponding confidence level may be determined that may be considered for determining the target anatomy. Further, the above-mentioned possibilities comprising the shift, weighting factors may also be applied in case of a plurality of landmarks.

In an embodiment, determining the position of the at least one landmark and determining the position of the target anatomy may be based on an image analysis algorithm. The analysis algorithm may comprise, for example, a segmentation algorithm, an artificial neural network, a deep convolutional neural network, an image acquisition model, and/or a model for determining confidence levels. In an embodiment, the analysis algorithm may use an image acquisition model that describes the process by which the obtained image of the series of images has been obtained. The image acquisition model may describe irregularities (e.g. alignment errors, rotation errors) occurring in the imaging process. As a result, the image acquisition model may generate from one input image (e.g. the first image of series of images) several output images that are indicative for irregularities. Based on the several output images a deep convolutional neuronal network may determine the landmarks in each of the several output images. The uncertainty may then be determined by calculating the entropy between input image and the several output images. A description of the image analysis algorithm, which may be used for the embodiments described in the present disclosure, is described in the article "Aleatoric uncertainty estimation with test-time augmentation for medical image segmentation with convolutional neural networks", written by Guotai Wang, Wenqi Li, Michael Aertsen, Jan Deprest, Sebastian Ourselin, Tom Vercauteren, and published by Neurocomputing, 2019, https://doi.org/10.1016/j.neucom.2019.01.103. The content of this article is incorporated by reference herein in its entirety.

In an embodiment, based on the determined position of the target anatomy a control signal for controlling an imaging unit may be derived. The position of the target anatomy may be a part of a control information of the imaging unit such as a MRI. This may be advantageous in terms of workflow efficiency, as no medical assistant has to do the calculation or related tasks. The method may further automate parts of the workflow of the medical assistant.

In an embodiment, based on the position of the target anatomy guidance data for preparing the subject in medical imaging may be derived and wherein the guidance data comprises a target alignment of the subject in relation to an imaging unit. The term guidance data means in the present case any data that is configured to guide a medical assistant to prepare a subject and/or a medical imaging unit for imaging. The guidance data may comprise visual representations of a target alignment of the medical equipment (e.g. a coil) that has to be aligned to the subject.

In an embodiment, determining of the position of the target anatomy is based on one or more degrees of freedom of one or more joints of the subject. The subject may comprise joints, bones, tissues, organs etc. that cannot move complete freely and independently of each other. The method may use a cinematic model comprising constraints for movement of parts of the subject. In particular, the method may consider degrees of freedom of joints. For example, a knee joint can only move in a range of 180°, otherwise the knee joint would break. As result this may increase the accuracy of determining the position of target anatomy due exclusion of unrealistic results (e.g. knee joint angle of 230°).

A further aspect of the present disclosure relates to a device for preparing a subject in medical imaging, comprising: an obtaining unit configured to obtain a series of images of a region of interest comprising at least a part of the subject, wherein the series of images comprises at least a first image and a subsequent, second image; a first determining unit configured to determine a position of at least one landmark from the series of images, wherein the at least one landmark is anatomically related to a target anatomy; a second determining unit configured to determine a confidence level assigned to the position of the at least one landmark;

a third determining unit configured to determine the position of the target anatomy based on the position of the at least one landmark and the confidence level; a providing unit configured to provide the position of the target anatomy for preparing the subject in medical imaging.

The obtaining unit and/or the determining units and/or the providing unit may be distributed on different hardware units or combined in a single hardware. The first determining unit and the second determining unit and the third determining unit may be one hardware unit. Further, the obtaining unit and/or the determining units and/or the providing unit may be virtual units (i.e. software units).

Optionally, the device may be configured to carry out the method according to the first aspect.

A further aspect of the present disclosure relates to an imaging system, comprising: a device described above; an imaging unit; an imaging control unit. The imaging unit may be a CT, MRI, and X-Ray imaging unit.

A further aspect of the present disclosure relates a computer program element, which when executed by a processor is configured to carry out the above described method, and/or to control an above described device, and/or to control a system described above.

The computer program element might be stored on a computer unit, which might also be part of an embodiment. This computing unit may be configured to perform or induce performing of the steps of the method described above. Moreover, it may be configured to operate the components of the above-described device. The computing unit can be configured to operate automatically and/or to execute the orders of a user. A computer program may be loaded into a working memory of a data processor. The data processor may thus be equipped to carry out the method according to one of the preceding embodiments. This exemplary embodiment of the invention covers both, a computer program that right from the beginning uses the invention and computer program that by means of an update turns an existing program into a program that uses invention. Further on, the computer program element might be able to provide all necessary steps to fulfill the procedure of an exemplary embodiment of the method as described above. According to a further exemplary embodiment of the present invention, a computer readable medium, such as a CD-ROM, USB stick or the like, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
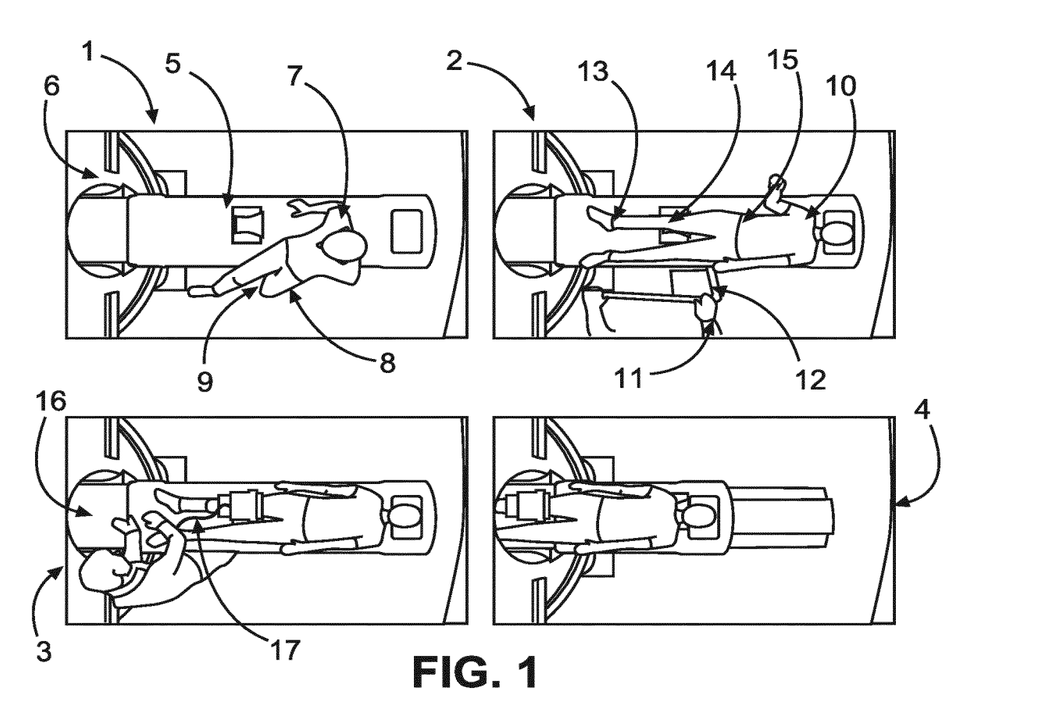
FIG. 1 shows exemplary images of a series of images according to a first embodiment of the present disclosure.

FIG. 1 shows exemplary images of a series of images according to a first embodiment of the present disclosure. The four images 1, 2, 3, and 4 all show the same scene, namely the preparation of a subject for medical imaging of the right knee of a patient at different stages in time. The image is obtained from a digital light camera (see e.g. FIG. 4, referred to as obtaining unit 41) implemented above the scene. In particular, image 1 shows a patient 7, who is just getting onto the patient support 5. The patient support 5 is part of a magnet resonance imaging unit 6. The patient support 5 is used for preparation of the patient outside a bore 7 of MRI unit 6. Once the patient 7 is prepared, the patient support 5 moves with the lying patient on it into the bore of the MRI unit 6. Afterwards, the medical imaging process for obtaining the medical MRI images starts. As can be seen in image 1 not all portions of the patient 7 are visible for the camera, e.g. the left foot 8 of the patient is hidden by the patient's left knee 9. Image 2 shows a further stage of the preparation. The patient 10 lies already on the patient support. A medical assistant 11 appears in the image 2 holding a coil 12 to be placed on the patient 10. As can be seen in image 2 nothing hides the portions of the patient 10 in this stage of preparation. There are no obstacles between the patient 10 and the camera implemented above. Hence, the field of view on to potential landmarks, such as right foot ankle 13, right hip 15 and target anatomy 14, namely the knee 14, of the camera is free. The landmarks, right foot ankle 13 and right hip 15, are anatomically connected to the target anatomy 15, the right knee 15. Hence, any movement of the landmarks influences the position of the target anatomy. For example, if the right foot ankle 13 moves laterally to left also the right knee 15 has to move laterally to left. In image 3, the medical assistant has nearly finished the placement of the coil on the right knee of the patient. In consequence, the right knee is hidden by the coil, such that there is no free field of view of the camera to the right knee. The right hip is clearly visible, but the right foot ankle is also slightly hidden by a cable 17 of the coil. In image 4, the patient support with patient onto it moves automatically into the bore 16 of the MRI. Hence, also the landmarks and target anatomy are no further visible for the camera.

Figure 2:
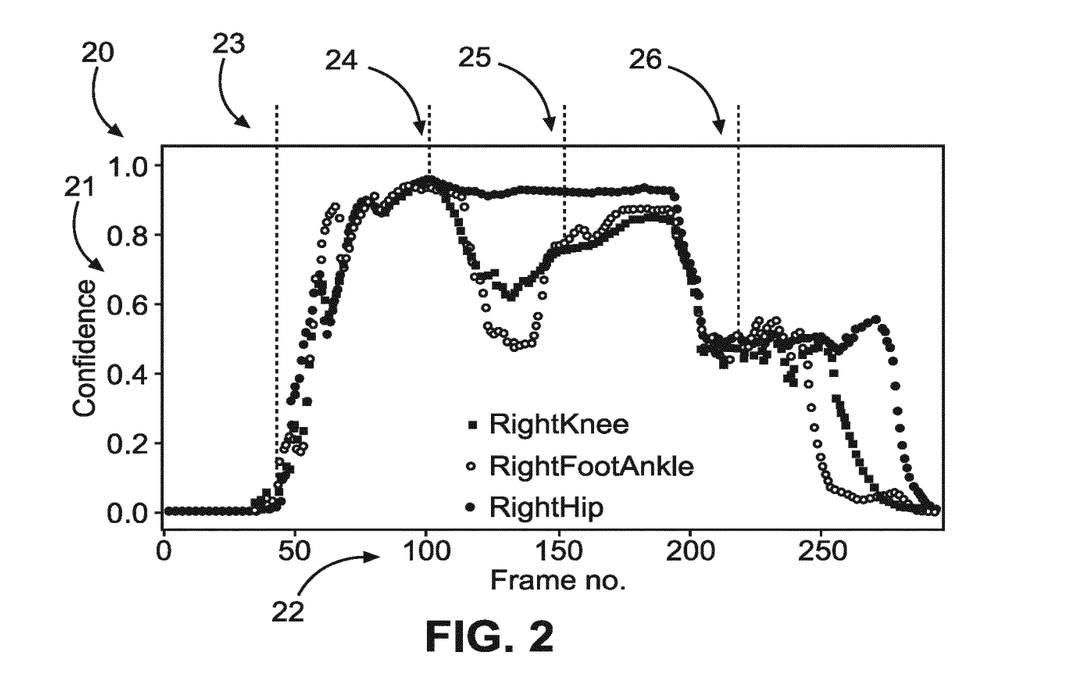
FIG. 2 shows a diagram of confidence levels over a series of images.

FIG. 2 shows a diagram of confidence levels over a series of images. FIG. 2 corresponds FIG. 1, wherein FIG. 1 relates to four images and FIG. 2 relates to 300 images and wherein the four images of FIG. 1 are part of the 300 images of FIG. 2. The confidence level is plotted on the vertical axis 21 of the diagram. The confidence level represents the reliability of a determined position. The confidence level comprises in this example values from 0 to 1, wherein decimal values like 0.81 are possible. The way how the confidence levels are determined will be explained in FIG. 3. The number of the respective picture is shown on the horizontal axis 22 of the diagram 21. For each image, the confidence levels of the right knee, or right foot ankle, or right hip are plotted respectively as points in the diagram. The vertical dotted lines 23, 24, 25 and 26 with the numbers 1 to 4 in brackets refer to the respective points in the diagram, which relate to the images 1 to 4 in FIG. 1. As can be seen the confidence levels in the first 50 images have values approximately around 0, due to absence of the landmarks or the target anatomy the images. In the range between 50 and 100 images, the confidence levels rise up to approximately 0.9.

This is due to the increased visibility of the landmarks and the target anatomy from first stage of the preparation, wherein the patient gets onto the patient support and to the second stage, wherein the patients lies on the patient support. In the range of 120 to 150 images, the confidence levels of the right knee and the right foot ankle decrease, due the placement of the coil by the medical assistant onto the right knee of the patient. The coil, the corresponding cable, and the medical assistant hide the right foot ankle and the right knee, which results in reduced confidence levels for each. The right hip is during the process not hidden by any obstacles such that the camera has a free field of view on the right hip. The free field of view on the right hip leads to a high confidence level of approximately 0.9. After finishing the positioning of the coil on the patient the confidence levels of the right foot ankle and the right knee raise slightly in the range of 150 to 200 images but do not reach previous high confidence level from 0.9 as the right hip has. This is due to the obstacles of the coil and corresponding cable. In the range of 200 to 300 images, confidence levels of both landmarks and target anatomy decrease as the patient moves with the patient support into the bore and is therefore invisible for the camera. As can be seen from the example the confidence level of the position of the region of interest, the right knee decreases during the preparation and the confidence level of one landmark, namely the right foot ankle. However, the second landmark, the right hip, remains visible and therefor the confidence level of the right hip has a high value until the patient moves into the bore.

Figure 3:
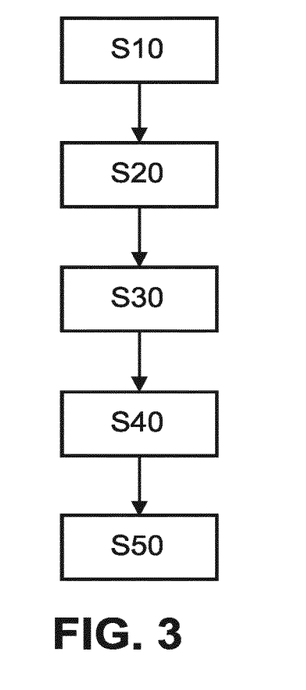
FIG. 3 is a schematic view of the method according to a first aspect of the present disclosure.

FIG. 3 is a schematic view of the method according to a first aspect of the present disclosure. 1. The computer-implemented method is used for preparing a subject in medical imaging. The subject is in the present case patient. The right knee of the patient shall be prepared for a MRI process. The right knee is in the present case the region of interest. The method comprises the following steps:

In a first step S10 a series of images of a region of interest comprising at least a part of the subject, wherein the series of images comprises at least a first image and at least a subsequent, second image is obtained. The images are obtained by a digital light camera that is implemented above a patient support on which the patient is positioned and prepared for the imaging process. In step S20 a position of at least one landmark from the series of images, wherein the at least one landmark is anatomically related to a target anatomy is obtained. The position is obtained by an image analysis algorithm, in particular an algorithm that is based on a deep neural network. The algorithm further comprises an image acquisition model that simulates the process by which the image is obtained. The model describes irregularities (e.g. alignment errors, rotation errors) occurring in the imaging process. As a result the image acquisition model generates from one obtained input image (e.g. the first image of series of images) several output images that are indicative for irregularities. Based on the several output images the deep convolutional neuronal network determines the position of the landmarks in each of the several output images. The average of the positions of the landmarks of the several output images serves then as position of the landmarks in the image. In step S30 a confidence level assigned to the position of the at least one landmark is obtained. The confidence level is determined by calculating the entropy between input image and the several output images. Alternatively, the confidence level is determined by calculating the deviation of the positions of the landmarks in the several output images. A description of the image analysis algorithm which may be used for step S10 to S30 described in the present disclosure, is described in the article "Aleatoric uncertainty estimation with test-time augmentation for medical image segmentation with convolutional neural networks", written by Guotai Wang, Wenqi Li, Michael Aertsen, Jan Deprest, Sebastian Ourselin, Tom Vercauteren, and published by Neurocomputing, 2019, https://doi.org/10.1016/j.neucom.2019.01.103. The content of this article is incorporated by reference herein in its entirety.

In step S40 the position of the target anatomy based on the position of the at least one landmark, and the confidence level is determined. In image 3 of FIG. 2 for example the position and confidence level of the foot ankle and the position and confidence level of the right hip are used to determine the position of right knee. As the confidence level of the foot ankle is below a predetermined threshold with the value 0.85, the position of the foot ankle in this image is not used for determining the position of the right knee. Instead, the position of the foot ankle in image 2 of FIG. 2 is used and the position of the right hip in image 3 of FIG. 2, as the confidence level of the position the right hip in image 3 is above the predetermined threshold. In other words, more than one image is used for the determining the position of the right knee in case that the confidence levels of the landmarks are not all above the predetermined threshold. In image 2 of FIG. 2 all confidence levels of the positions are above the predetermined threshold and therefor only one image is used for determining the position of the right knee. Alternatively, also further previous images can be used to determine the position of the right knee. This might be useful in order to increase the reliability. Further, it shall be noticed that in this example, the position of the right knee is also obtained with a neural network and therefor a confidence level is determined as described above. In other examples or applications, the target anatomy is not visible such as organs like the liver. The position of the liver has to be determined by landmarks and cannot be determined otherwise. In a step S50, the position of the target anatomy for preparing the subject in medical imaging is provided. The information of the position of target anatomy may be transmitted to a control of the imaging system or the imaging unit. The information of the position of the target anatomy may displayed on a screen to guide a medical assistant.

Figure 4:
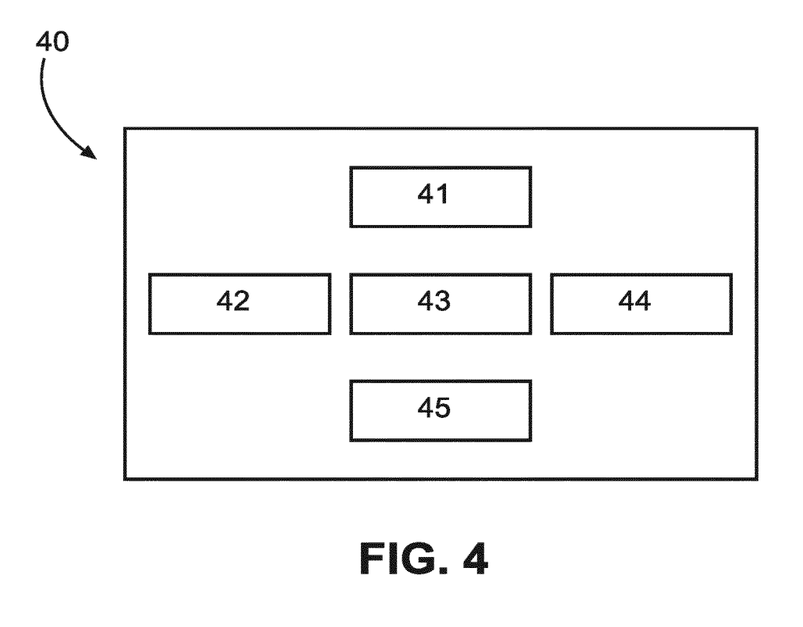
FIG. 4 is schematic view of a device according to a further aspect of the present disclosure.

FIG. 4 is schematic view of device according to an embodiment of the present disclosure. The device 40 for preparing a subject in medical imaging, comprises an obtaining unit 41 configured to obtain a series of images of a region of interest comprising at least a part of the subject, wherein the series of images comprises at least a first image and a subsequent, second image; a first determining unit 42 configured to determine a position of at least one landmark from the series of images, wherein the at least one landmark is anatomically related to a target anatomy; a second determining unit 43 configured to determine a confidence level assigned to the position of the at least one landmark; a third determining unit 44 configured to determine the position of the target anatomy based on the position of the at least one landmark and the confidence level; a providing unit 45 configured to provide the position of the target anatomy for preparing the subject in medical imaging.

LIST OF REFERENCE SIGNS 1, 2, 3, 4 image
5 patient support
6 imaging unit
7, 10 patient
8 left foot 9 left knee
11 medical assistant
12 coil
13 right foot ankle, landmark
14 right knee, target anatomy
15 right hip, landmark
16 bore
17 cable
20 diagram
21 vertical axis
22 horizontal axis
23, 24, 25, 26 vertical dotted lines
40 device
41 obtaining unit
42 first determining unit
43 second determining unit
44 second determining unit
45 providing unit

The invention claimed is:

1. A computer-implemented method for preparing a subject in medical imaging, comprising:
   obtaining a series of images of a region of interest comprising at least a part of the subject, wherein the series of images comprises at least a first image and at least a subsequent, second image;
   determining a position of at least one landmark from the series of images, wherein the at least one landmark is anatomically related to a target anatomy;
   determining a confidence level assigned to the position of the at least one landmark;
   determining the position of the target anatomy based on the position of the at least one landmark in the series of images, and the confidence level over the series of images; and
   providing the position of the target anatomy for preparing the subject in medical imaging wherein based on the determined confidence level a weighting factor for a shift of the position of the at least one landmark is determined, and wherein the weighting factor is used for determining the position of the target anatomy.

2. The method according to claim 1, wherein the position of the target anatomy is, in case that the confidence level of the at least one landmark in the second image is below a predetermined threshold, determined from the at least one landmark in the first image.

3. The method according to claim 1, wherein determining the position of the target anatomy comprises further determining a shift of the position of the at least one landmark between the first image and the second image.

4. The method according to claim 1, wherein the position of the target anatomy is, in case that the confidence level of the at least one landmark in the second image is above the predetermined threshold, determined
   either from a shift of the position of the at least one landmark between the first image and the second image,
   or from the at least one landmark in the second image.

5. The method according to claim 1, wherein the at least one landmark is selected in dependency of a presence of the landmark in the series of images.

6. The method according to claim 1, wherein the target anatomy is hidden by an obstacle.

7. The method according to claim 1, wherein the position of the target anatomy is derived from a plurality of landmarks.

8. The method according to claim 1, wherein determining the position of the at least one landmark and determining the position of the target anatomy is based on an image analysis algorithm.

9. The method according to claim 1, wherein based on the determined position of the target anatomy a control signal for controlling an imaging unit is derived.

10. The method according to claim 1, wherein based on the position of the target anatomy guidance data for preparing the subject in medical imaging is derived and wherein the guidance data comprises a target alignment of the subject in relation to an imaging unit.

11. The method according to claim 1, wherein determining of the position of the target anatomy is based on one or more degrees of freedom of one or more joints of the subject.

12. A device for preparing a subject in medical imaging, comprising:
    an obtaining unit configured to obtain a series of images of a region of interest comprising at least a part of the subject, wherein the series of images comprises at least a first image and a subsequent, second image;
    a first determining unit configured to determine a position of at least one landmark from the series of images, wherein the at least one landmark is anatomically related to a target anatomy;
    a second determining unit configured to determine a confidence level assigned to the position of the at least one landmark;
    a third determining unit configured to determine the position of the target anatomy based on the position of the at least one landmark in the series of images and the confidence level over the series of images; and
    a providing unit configured to provide the position of the target anatomy for preparing the subject in medical imaging wherein based on the determined confidence level a weighting factor for a shift of the position of the at least one landmark is determined, and wherein the weighting factor is used for determining the position of the target anatomy.

13. An imaging system, comprising:
    a device according to claim 12;
    an imaging unit;
    an imaging control unit.

14. A computer program element, comprising executable instructions stored on a non-transitory computer readable medium which when executed by a processor causes the processor to:
    obtain a series of images of a region of interest comprising at least a part of the subject, wherein the series of images comprises at least a first image and at least a subsequent, second image;
    determine a position of at least one landmark from the series of images, wherein the at least one landmark is anatomically related to a target anatomy;
    determine a confidence level assigned to the position of the at least one landmark;
    determine the position of the target anatomy based on the position of the at least one landmark in the series of images, and the confidence level over the series of images; and
    provide the position of the target anatomy for preparing the subject in medical imaging wherein based on the determined confidence level a weighting factor for a shift of the position of the at least one landmark is determined, and wherein the weighting factor is used for determining the position of the target anatomy.

15. The computer program element according to claim 14, wherein the position of the target anatomy is, in case that the confidence level of the at least one landmark in the second image is below a predetermined threshold, determined from the at least one landmark in the first image.

16. The computer program element according to claim 14, wherein when determining the position of the target anatomy, the instructions further cause the processor to determine a shift of the position of the at least one landmark between the first image and the second image.

17. The computer program element according to claim 14, wherein the position of the target anatomy is, in case that the confidence level of the at least one landmark in the second image is above the predetermined threshold, determined
- either from a shift of the position of the at least one landmark between the first image and the second image,
- or from the at least one landmark in the second image.

18. The computer program element according to claim 14, wherein the at least one landmark is selected in dependency of a presence of the landmark in the series of images.

19. The computer program element according to claim 14, wherein the target anatomy is hidden by an obstacle.

20. The computer program element according to claim 14, wherein the position of the target anatomy is derived from a plurality of landmarks.

* * * * *